(12) United States Patent
McMorrow et al.

(10) Patent No.: US 8,712,542 B2
(45) Date of Patent: Apr. 29, 2014

(54) DEPOSITED CONDUCTIVE LAYERS FOR LEADS OF IMPLANTABLE ELECTRIC STIMULATION SYSTEMS AND METHODS OF MAKING AND USING

(75) Inventors: David Michael McMorrow, Galway (IE); Anne M. Pianca, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1201 days.

(21) Appl. No.: 12/264,526

(22) Filed: Nov. 4, 2008

(65) Prior Publication Data

US 2010/0114278 A1 May 6, 2010

(51) Int. Cl.
*A61N 1/00* (2006.01)
*H01B 7/00* (2006.01)
*H01B 11/02* (2006.01)

(52) U.S. Cl.
USPC ............ 607/116; 607/117; 607/118; 607/119; 174/113 R

(58) Field of Classification Search
USPC ................. 607/116–119; 174/113 R, 113
See application file for complete search history.

(56) References Cited

U.S. PATENT DOCUMENTS

| | | | |
|---|---|---|---|
| 4,317,278 A | 3/1982 | Carmon et al. | |
| 4,362,165 A | 12/1982 | Carmon et al. | |
| 4,837,049 A * | 6/1989 | Byers et al. | 216/6 |
| 5,016,633 A | 5/1991 | Chow | |
| 6,181,969 B1 | 1/2001 | Gord | |
| 6,208,881 B1 | 3/2001 | Champeau | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 6,749,556 B2 | 6/2004 | Banik | |
| 6,829,498 B2 | 12/2004 | Kipke et al. | |
| 6,921,360 B2 | 7/2005 | Banik | |
| 7,128,707 B2 | 10/2006 | Banik | |

(Continued)

FOREIGN PATENT DOCUMENTS

| | | |
|---|---|---|
| WO | WO-01/72201 A2 | 10/2001 |
| WO | WO-01/73864 A2 | 10/2001 |

(Continued)

OTHER PUBLICATIONS

U.S. Appl. No. 11/238,240, filed Sep. 29, 2005 (20 pages).

*Primary Examiner* — Niketa Patel
*Assistant Examiner* — Lindsey G Hankins
(74) *Attorney, Agent, or Firm* — Frommer Lawrence & Haug LLP; Patrick R. Turner

(57) ABSTRACT

An implantable lead includes an inner core substrate. A plurality of conductors that include at least one layer of at least one conductive material are deposited on the inner core substrate. A patterned insulator layer is disposed over the conductors such that at least two regions of each conductor remain exposed through the insulator. A patterned terminal layer defines a plurality of separated terminals that are deposited at a proximal end of the lead. At least one terminal is electrically coupled to each conductor via at least one of the exposed regions of the at least one conductor. A patterned electrode layer defines a plurality of separated electrodes that are deposited at a distal end of the lead. At least one electrode is electrically coupled to each conductor via at least one of the exposed regions of the at least one conductor.

20 Claims, 8 Drawing Sheets

(56) References Cited

U.S. PATENT DOCUMENTS

| | | |
|---|---|---|
| 7,244,150 B1 | 7/2007 | Brase et al. |
| 7,390,650 B2 | 6/2008 | Karlsson et al. |
| 7,456,012 B2 | 11/2008 | Ryttsen et al. |
| 7,470,518 B2 | 12/2008 | Chiu et al. |
| 2001/0023368 A1* | 9/2001 | Black et al. ............... 607/122 |
| 2001/0032666 A1 | 10/2001 | Jenson et al. |
| 2002/0001747 A1 | 1/2002 | Jenson et al. |
| 2003/0100823 A1 | 5/2003 | Kipke et al. |
| 2003/0114905 A1 | 6/2003 | Kuzma |
| 2003/0212306 A1 | 11/2003 | Banik |
| 2004/0015194 A1* | 1/2004 | Ransbury et al. ........... 607/10 |
| 2004/0110307 A1 | 6/2004 | Karlsson et al. |
| 2004/0230277 A1* | 11/2004 | Schell ........................ 607/122 |
| 2005/0004425 A1 | 1/2005 | Banik |
| 2005/0045223 A1 | 3/2005 | Jenson et al. |
| 2005/0048651 A1 | 3/2005 | Ryttsen et al. |
| 2005/0165465 A1 | 7/2005 | Pianca et al. |
| 2005/0256367 A1 | 11/2005 | Banik |
| 2006/0078961 A1 | 4/2006 | Chiu et al. |
| 2006/0184092 A1 | 8/2006 | Atanasoska et al. |
| 2006/0200218 A1* | 9/2006 | Wahlstrand ................. 607/116 |
| 2006/0212096 A1 | 9/2006 | Stevenson |
| 2006/0223164 A1 | 10/2006 | Orwar et al. |
| 2006/0234298 A1 | 10/2006 | Chiu et al. |
| 2007/0011399 A1 | 1/2007 | Dahman et al. |
| 2007/0043256 A1 | 2/2007 | Banik |
| 2007/0112398 A1 | 5/2007 | Stevenson et al. |
| 2007/0123949 A1 | 5/2007 | Dabney et al. |
| 2007/0150007 A1 | 6/2007 | Anderson et al. |
| 2007/0150036 A1 | 6/2007 | Anderson |
| 2007/0161294 A1 | 7/2007 | Brase et al. |
| 2007/0219595 A1 | 9/2007 | He |
| 2007/0239243 A1 | 10/2007 | Moffitt et al. |
| 2008/0049376 A1 | 2/2008 | Stevenson et al. |
| 2008/0065181 A1 | 3/2008 | Stevenson |
| 2008/0071313 A1 | 3/2008 | Stevenson et al. |
| 2008/0116997 A1 | 5/2008 | Dabney et al. |
| 2008/0125838 A1 | 5/2008 | Francis |
| 2008/0132987 A1 | 6/2008 | Westlund et al. |
| 2008/0161886 A1 | 7/2008 | Stevenson et al. |
| 2008/0195180 A1 | 8/2008 | Stevenson et al. |
| 2008/0262412 A1 | 10/2008 | Atanasoska et al. |

FOREIGN PATENT DOCUMENTS

| | | | |
|---|---|---|---|
| WO | WO-01/73870 A2 | 10/2001 | |
| WO | WO-03/068906 A1 | 8/2003 | |
| WO | WO-03/094800 A2 | 11/2003 | |
| WO | WO-2004/018690 A1 | 3/2004 | |
| WO | WO-2006/074350 A2 | 7/2006 | |
| WO | WO-2006/086672 A1 | 8/2006 | |
| WO | WO-2006/131912 A2 | 12/2006 | |
| WO | WO-2007/039783 A2 | 4/2007 | |
| WO | WO-2007/117302 A2 | 10/2007 | |
| WO | WO-2007/120884 A2 | 10/2007 | |
| WO | WO-2008/072029 A2 | 6/2008 | |
| WO | WO 2008081181 A1 * | 7/2008 | ............ G01N 29/02 |

* cited by examiner

DEPOSITED CONDUCTIVE LAYERS FOR LEADS OF IMPLANTABLE ELECTRIC STIMULATION SYSTEMS AND METHODS OF MAKING AND USING

TECHNICAL FIELD

The present invention is directed to the area of implantable electrical stimulation systems and methods of making and using the systems. The present invention is also directed to implantable electrical stimulation systems including leads with patterned conductive layers deposited onto the leads, as well as methods of making and using the leads and implantable electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Deep brain stimulation has also been useful for treating refractory chronic pain syndromes and has been applied to treat movement disorders and epilepsy. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Moreover, electrical stimulation systems can be implanted subcutaneously to stimulate subcutaneous tissue including subcutaneous nerves such as the occipital nerve.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, an implantable lead includes a lead body with a distal end, a proximal end, and an inner core substrate. The implantable lead also includes a plurality of conductors disposed on the inner core substrate, a patterned insulator layer disposed over the conductors, a patterned terminal layer, and a patterned electrode layer. Each conductor includes at least one layer of at least one conductive material deposited on the inner core substrate. The patterned insulator layer is disposed over the conductors such that at least two regions of each conductor remain exposed through the insulator, including at least one region in proximity to the proximal end and at least one region in proximity to the distal end. The patterned terminal layer defines a plurality of separated terminals that are deposited at the proximal end of the lead body. At least one terminal is electrically coupled to each conductor via at least one of the regions of the at least one conductor exposed through the patterned insulator layer in proximity to the proximal end. The patterned electrode layer defines a plurality of separated electrodes that are deposited at the distal end of the lead body. At least one electrode is electrically coupled to each conductor via at least one of the regions of the at least one conductor exposed through the patterned insulator layer in proximity to the distal end.

In another embodiment, an electrical stimulating system includes a lead, a control module, and a connector. The lead has a distal end, a proximal end, and an inner core substrate. The lead also includes a plurality of conductors disposed on the inner core substrate, a patterned insulator layer disposed over the conductors, a patterned terminal layer, and a patterned electrode layer. Each conductor includes at least one layer of at least one conductive material deposited on the inner core substrate. The patterned insulator layer is disposed over the conductors such that at least two regions of each conductor remain exposed through the insulator, including at least one region in proximity to the proximal end and at least one region in proximity to the distal end. The patterned terminal layer defines a plurality of separated terminals that are deposited at the proximal end of the lead body. At least one terminal is electrically coupled to each conductor via at least one of the regions of the at least one conductor exposed through the patterned insulator layer in proximity to the proximal end. The patterned electrode layer defines a plurality of separated electrodes that are deposited at the distal end of the lead body. At least one electrode is electrically coupled to each conductor via at least one of the regions of the at least one conductor exposed through the patterned insulator layer in proximity to the distal end. The control module is configured and arranged to electrically couple to the proximal end of the lead. The control module includes a housing and an electronic subassembly disposed in the housing. The connector is configured and arranged for receiving the lead. The connector has a proximal end, a distal end, and a longitudinal length. The connector includes a connector housing and a plurality of conductive contacts. The connector housing defines a port at the distal end of the connector. The port is configured and arranged for receiving the proximal end of the lead. The conductive contacts are configured and arranged to couple to at least one of the plurality of terminals disposed on the proximal end of the lead.

In yet another embodiment, a method for making an implantable lead includes depositing a plurality of conductors along at least a portion of a longitudinal length of an inner core substrate of a lead body. A patterned insulator layer is disposed over the conductors such that at least two regions of each conductor remains exposed through the insulator, including at least one region in proximity to a proximal end of the lead body and at least one region in proximity to a distal end of the lead body. A patterned terminal layer, defining a plurality of separated terminals, is deposited at the proximal end of the lead body so that each of the separated terminals electrically couples to at least one of the conductors exposed through at least one exposed region of each conductor in proximity to the proximal end of the lead. A patterned electrode layer, defining a plurality of separated electrodes, is deposited at the distal end of the lead so that each of the separated electrodes electrically couples to at least one of the conductors via at least one exposed regions of each conductor in proximity to the distal end of the lead.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation systems including leads with patterned conductive layers deposited onto the leads, as well as methods of making and using the leads and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; and U.S. patent application Ser. Nos. 10/353,101, 10/503,281, 11/238,240; 11/319,291; 11/327,880; 11/375,638; 11/393,991; and 11/396,309, all of which are incorporated by reference.

Figure 1:
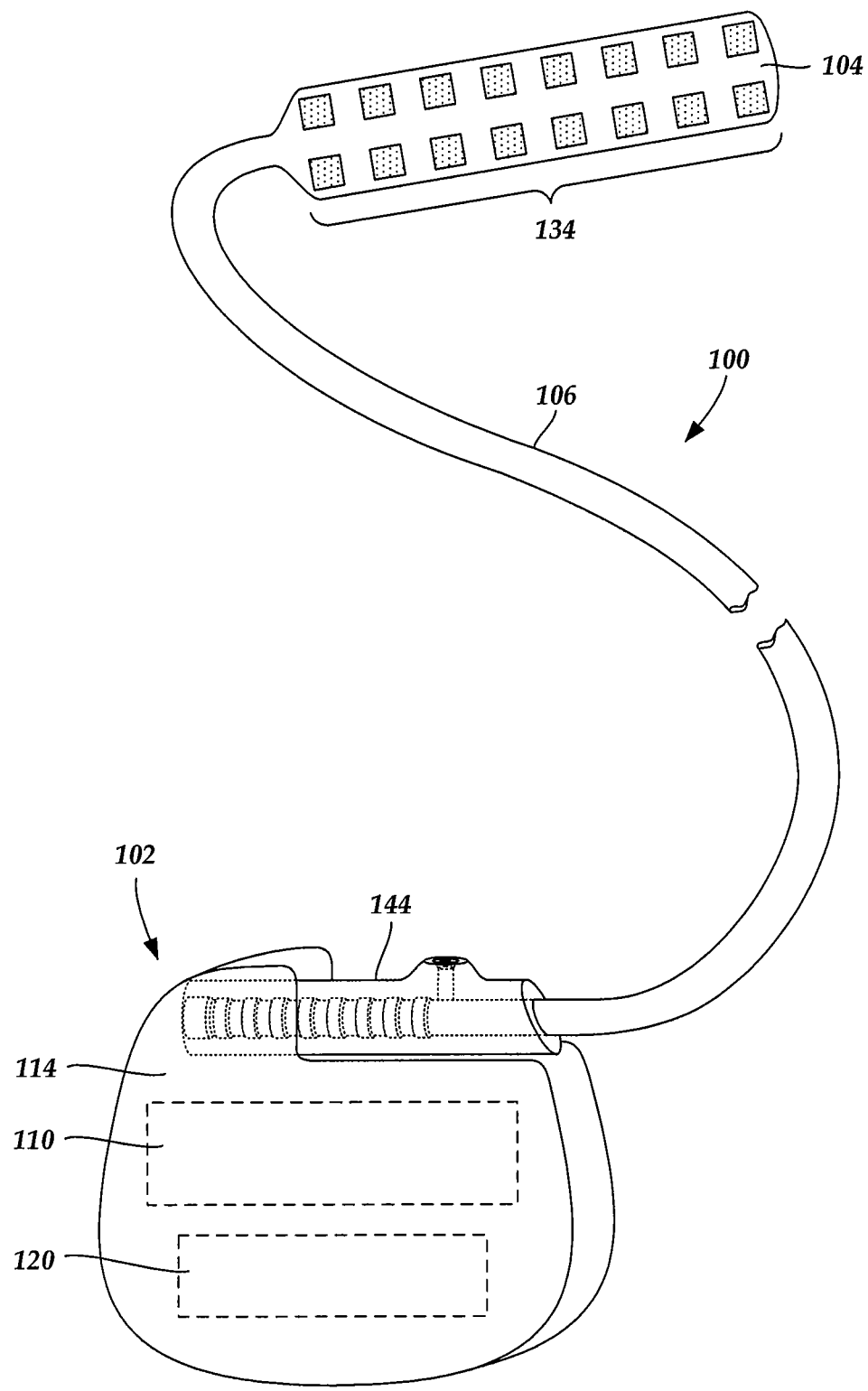
FIG. 1 is a schematic view of one embodiment of an electrical stimulation system, according to the invention.
Figure 2:
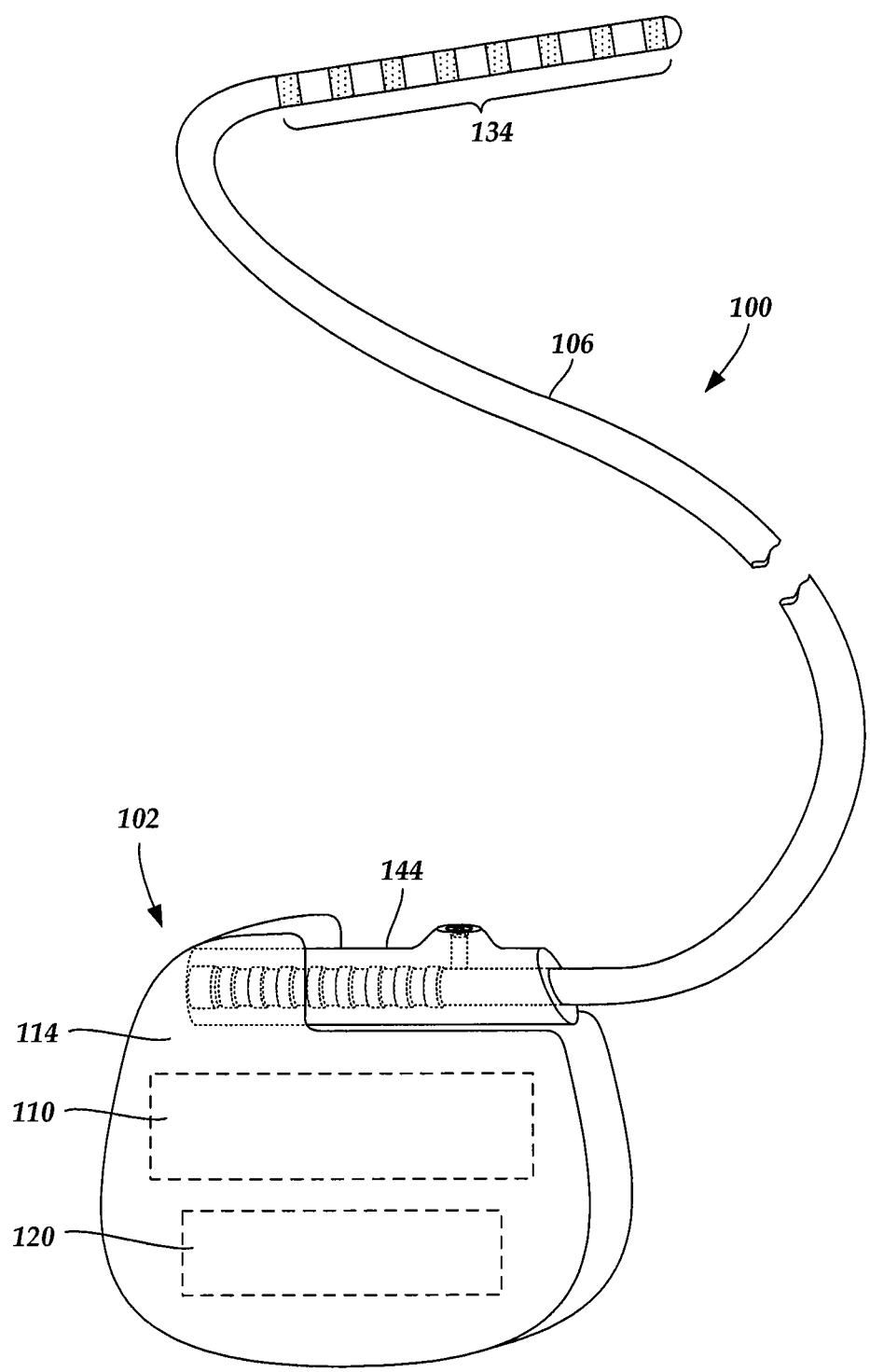
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144 (FIGS. 2 and 3A, see also 322 and 350 of FIG. 3B) into which the proximal end of the one or more lead bodies 106 can be plugged to make an electrical connection via conductive contacts on the control module 102 and terminals (e.g., 310 in FIG. 3A and 336 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 312 (see FIG. 3B) can be disposed between the one or more lead bodies 106 and the control module 102 to extend the distance between the one or more lead bodies 106 and the control module 102 of the embodiments shown in FIGS. 1 and 2.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material including, for example, silicone, polyurethane, polyetheretherketone ("PEEK"), epoxy, and the like or combinations thereof. The paddle body 104 and one or more lead bodies 106 may be formed in the desired shape by any process including, for example, molding (including injection molding), casting, and the like. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A and 336 of FIG. 3B) are typically disposed at the proximal end of the one or more lead bodies 106 for connection to corresponding conductive contacts (e.g., 314 in FIG. 3A and 340 of FIG. 3B) in connectors (e.g., 144 in FIGS. 1-3A and 322 and 350 of FIG. 3B) disposed on, for example, the control module 102 (or to other devices, such as conductive contacts on a lead extension, an operating room cable, or an adaptor). Conductors (not shown) extend from the terminals (e.g., 310 in FIG. 3A and 336 of FIG. 3B) to the electrodes 134. Typically, one or more electrodes 134 are electrically coupled to a terminal (e.g., 310 in FIG. 3A and 336 of FIG. 3B). In some embodiments, each terminal (e.g., 310 in FIG. 3A and 336 of FIG. 3B) is only connected to one electrode 134. There may also be one or more lumens (not shown) that open at, or near, the proximal end of the lead, for example, for inserting a stylet rod to facilitate placement of the lead within an body of a patient.

Figure 3A:
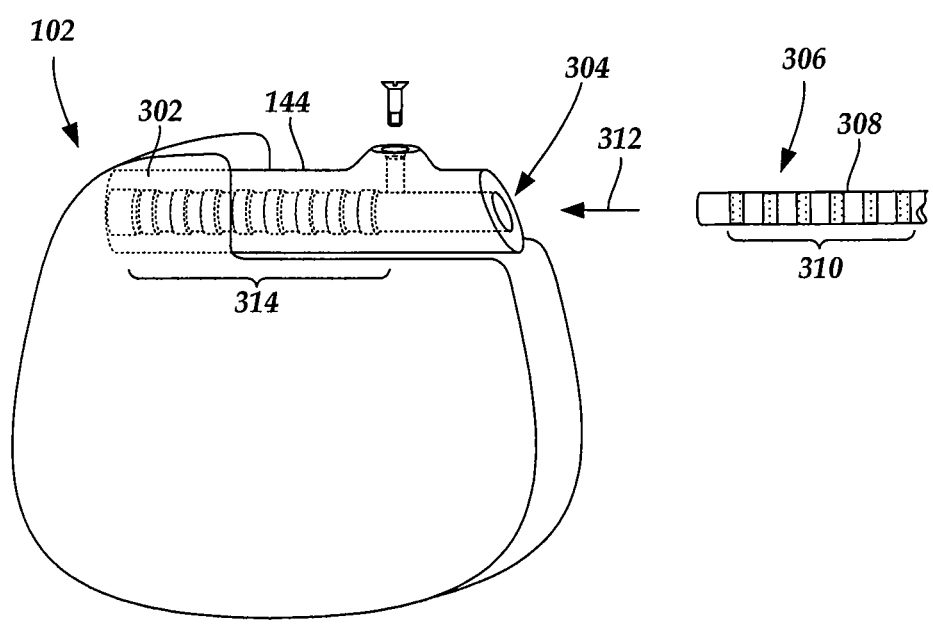
FIG. 3A is a schematic view of one embodiment of a proximal portion of a lead and a control module of an electrical stimulation system, according to the invention.

In at least some embodiments, leads are coupled to connectors disposed on control modules. In FIG. 3A, a lead 308 is shown configured and arranged for insertion to the control module 102. The connector 144 includes a connector housing 302. The connector housing 302 defines at least one port 304 into which a proximal end 306 of a lead 308 with terminals 310 can be inserted, as shown by directional arrow 312. The connector housing 302 also includes a plurality of conductive contacts 314 for each port 304. When the lead 308 is inserted into the port 304, the conductive contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat. No. 7,244,150 and U.S. patent application Ser. No. 11/532,844, which are incorporated by reference.

Figure 3B:
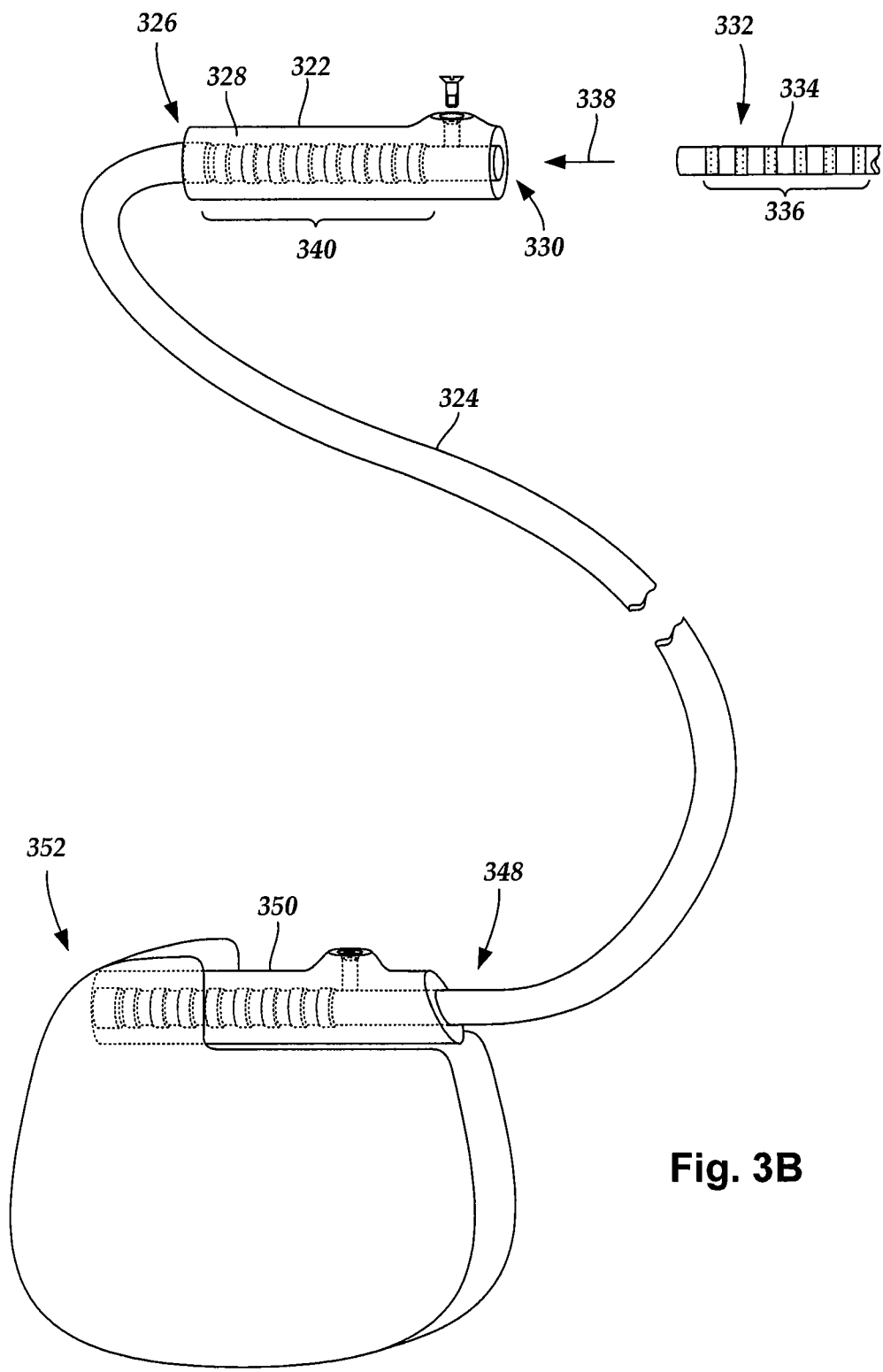
FIG. 3B is a schematic view of one embodiment of a proximal portion of a lead and a lead extension of an electrical stimulation system, according to the invention.

In FIG. 3B, a connector 322 is disposed on a lead extension 324. The connector 322 is shown disposed at a distal end 326 of the lead extension 324. The connector 322 includes a connector housing 328. The connector housing 328 defines at least one port 330 into which a proximal end 332 of a lead 334 with terminals 336 can be inserted, as shown by directional arrow 338. The connector housing 328 also includes a plurality of conductive contacts 340. When the lead 334 is inserted into the port 330, the conductive contacts 340 disposed in the connector housing 328 can be aligned with the terminals 336 on the lead 334 to electrically couple the lead extension 324 to the electrodes (134 of FIG. 1) disposed at a distal end (not shown) of the lead 334.

In at least some embodiments, the proximal end of a lead extension is similarly configured and arranged as a proximal end of a lead. The lead extension 324 may include a plurality of conductive wires (not shown) that electrically couple the conductive contacts 340 to a proximal end 348 of the lead extension 324 that is opposite to the distal end 326. In at least some embodiments, the conductive wires disposed in the lead extension 324 can be electrically coupled to a plurality of terminals (not shown) disposed on the proximal end 348 of the lead extension 324. In at least some embodiments, the terminals (not shown) are disposed on an outer lead-extension covering 350, which extends from the connector 322 to the proximal end 348. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. As an example, in FIG. 3B the proximal end 348 of the lead extension 324 is inserted into a connector 352 disposed in a control module 354.

It is often desirable for leads (and lead extensions) to have a transverse cross-sectional area that is as small and flexible as possible in order to increase the numbers and types of anatomical regions of a patient into which a lead (or a lead extension) may be inserted. Some conventional leads utilize a lead body that includes a central lumen and one or more conductor lumens arranged around the central lumen and extending along at least a portion of the longitudinal length of the lead. Typically, the central lumen is configured and arranged to receive a stylet for facilitating insertion of the lead into a patient, and the surrounding conductor lumens are configured and arranged to house one or more conductors that electrically couple one or more electrodes disposed at a distal end of the lead to one or more terminals disposed at a proximal end of the lead.

In at least some embodiments, a lead is described with at least one conductive layer deposited onto an inner core substrate of the lead to form a conductor. In at least some embodiments, one or more non-conductive materials are disposed over at least one of the conductors so that the conductor includes at least one region exposed through the one or more non-conductive materials in proximity to the proximal end and at least one region exposed through the one or more non-conductive materials in proximity to the distal end of the lead. In at least some embodiments, a patterned terminal layer is deposited over at least one exposed region of the conductor in proximity to the proximal end of the lead. In at least some embodiments, a patterned electrode layer is deposited over at least one exposed region of the conductor in proximity to the distal end of the lead. In at least some embodiments, the inner core substrate is disposed directly over a central lumen.

Figure 4:
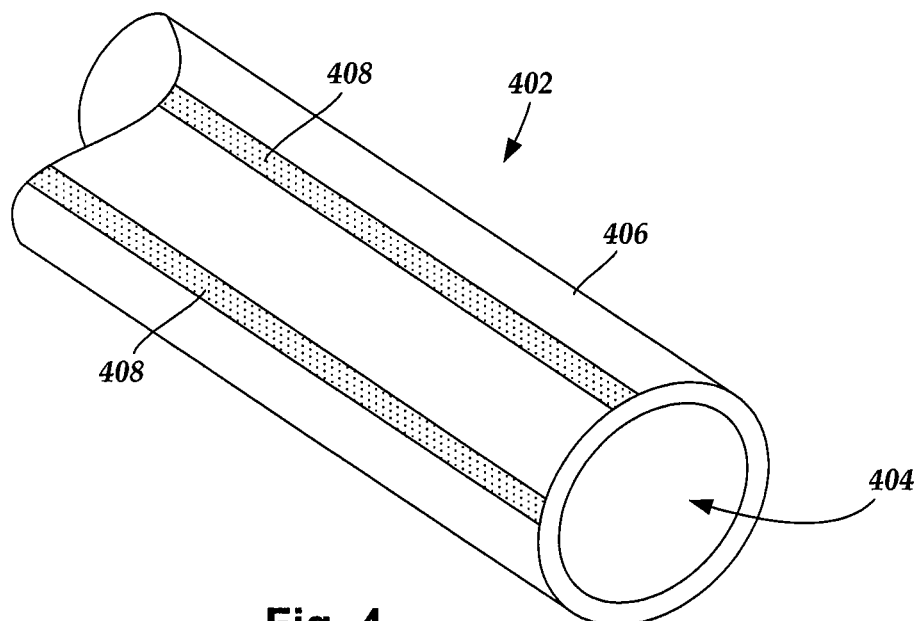
FIG. 4 is a schematic perspective view of one embodiment of a portion of a proximal end of a lead with conductive layers deposited on an inner core substrate of the lead to form conductors, according to the invention.

FIG. 4 is a schematic perspective view of one embodiment of a portion of a proximal end of a lead 402. The lead 402 includes a central lumen 404 and an inner core substrate 406. One or more conductive layers are deposited onto the inner core substrate 406 to form at least two conductors 408. In at least some embodiments, the conductors 408 extend along at least a portion of a longitudinal length of the lead 402.

The inner core substrate 406 may be formed of any suitable non-conductive, biocompatible material including, for example, silicone, polyurethane, PEEK, epoxy, polyimide, polysulphone, Teflon®, and the like or combinations thereof. The conductors 408 may be formed of any suitable biocompatible material suitable for implantation into a patient using a deposition process including, for example, gold, platinum, platinum/iridium, stainless steel, MP35N, and the like or combinations thereof.

In some embodiments, the conductors 408 are deposited as a single conductive layer. In other embodiments, the conductors 408 are deposited in multiple conductive layers. In at least some embodiments, each of the one or more conductive layers forming the conductors 408 have a thickness no greater than one micrometer. In at least some embodiments, each conductive layer has a thickness no greater than one hundred nanometers. In at least some embodiments, the conductors 408 are formed using a metal deposition process. In at least some embodiments, the conductors 408 are formed using a magnetron sputtering process, physical or chemical vapor deposition, or the like. The conductors 408 may be patterned after deposition or simultaneously with deposition. In at least some embodiments, the conductors 408 and 410 are formed directly on the inner core substrate 406. In other embodiments, the conductors 408 and 410 are formed on one or more intermediate layers which, in turn, are disposed on the inner core substrate 406.

Any suitable number of conductors may be formed on the inner core substrate 406. For example, there may be one, two, three, four, five, six, seven, eight, nine, ten, eleven, twelve, sixteen, twenty-four, thirty-two, or more conductors formed on the inner core substrate 406. It will be understood that other numbers of conductors may be formed on the inner core substrate 406. In at least some embodiments, the number of conductors formed on the inner core substrate 406 is proportional to the number of electrodes or terminals disposed on the lead 402. In at least some embodiments, the number of conductors formed on the inner core substrate 406 is equal to the number of electrodes or terminals disposed on the lead 402.

In at least some embodiments, the central lumen 404 is configured and arranged to receive a stylet for facilitating insertion of the lead 402 into a patient. In at least some embodiments, the lead 402 includes at least one additional lumen (not shown in FIG. 4). In at least one embodiment, the at least one additional lumen opens at, or near, a distal end of the lead, for example, for infusion of drugs or medication into the site of implantation of the lead 402. In at least one embodiment, the at least one additional lumen may be flushed continually, or on a regular basis, with saline, epidural fluid, or the like. In at least some embodiments, the at least one additional lumen can be permanently or removably sealable at the distal end of the lead 402.

In at least some embodiments, depositing layers of conductive material onto the inner core substrate 406 may eliminate the need for disposing conductors into conductor lumens arranged around the central lumen 404. Consequently, in at least some embodiments the diameter of the lead 402 with deposited layers of conductive material may be less than the diameter of a lead with one or more conductor lumens arranged around a central lumen. Additionally, the lead 402 with deposited conductors may also be more flexible than a lead with conductors disposed in conductor lumens. Moreover, forming conductors by depositing layers of conductive material on the inner core substrate 406 may allow the lead 402 to achieve a higher density of conductors than leads with conductors disposed in conductor lumens.

Figure 5:
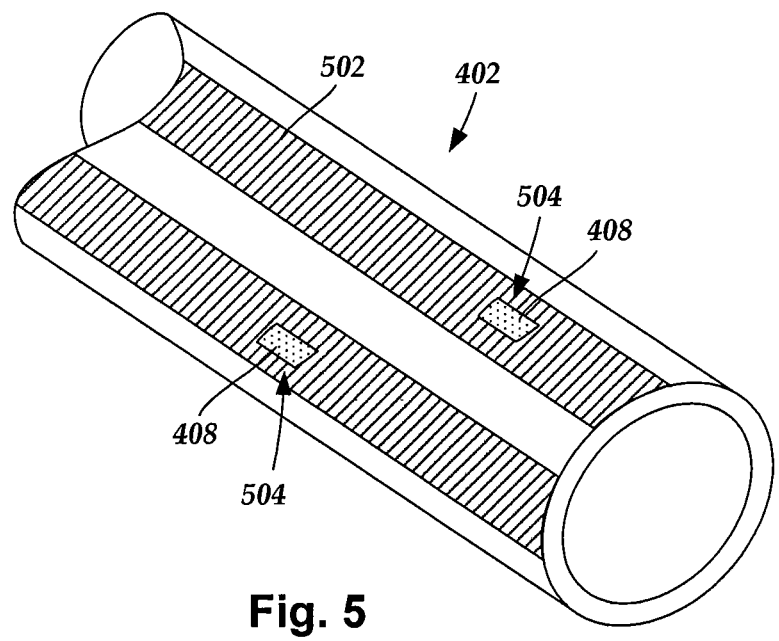
FIG. 5 is a schematic perspective view of one embodiment of a portion of a proximal end of the lead shown in FIG. 4 with a patterned insulator layer disposed over two conductors so that a region of the covered conductors remain exposed through the insulator layer, according to the invention.

In at least some embodiments, once the conductors 408 are formed on the inner core substrate 406 of the lead 402, at least a portion of the conductors 408 can be insulated by disposing one or more layers of one or more non-conductive materials ("insulating layer") over at least a portion of the conductors 408. FIG. 5 is a schematic perspective view of one embodiment of a portion of a proximal end of the lead 402. The lead 402 includes at least one patterned insulator layer 502 disposed over at least two of the conductors 408. The patterned insulator layer 502 is disposed over the conductors 408 so that the conductors 408 each include a region 504 exposed through the patterned insulator layer 502 in proximity to the proximal end of the lead 402. In at least some embodiments, the patterned insulator layer 502 is disposed over the conductors 408 so that the conductors 408 include a plurality of regions exposed through the patterned insulator layer 502 along the length of each conductor 408. In some embodiments, the patterned insulator layer 502 is disposed over each conductor individually. In other embodiments, the patterned insulator layer 502 is disposed over a plurality of conductors concurrently. The insulator layer 502 may be patterned after deposition or simultaneously with deposition, using any known patterning technique.

Any suitable non-conductive material may be used to form the one or more patterned insulator layers 502 including, for example, one or more non-conductive polymers, silicone, polyurethane, PEEK, polyimide, epoxy, polysulphone, Teflon®, and the like or combinations thereof. The one or more patterned insulator layers 502 disposed over the conductor 408 may be applied to the lead 402 using any suitable deposition technique including, for example, spray coating, ink jet printing, dipping, sputtering, physical or chemical vapor deposition, and the like or combinations thereof.

In at least some embodiments, once the one or more patterned insulator layers 502 are disposed over one or more conductors, one or more patterned terminal layers may be disposed on the lead to form one or more terminals. In at least some embodiments, one or more terminals may be electrically coupled to each of the conductors disposed beneath the patterned insulator layer. In at least some embodiments, one or more terminals may be electrically coupled to each of the conductors via one or more regions of the conductors exposed through the patterned insulator layer. In at least some embodiments, one or more terminals may be deposited on the lead such that at least a portion of each terminal is deposited over at least a portion of the patterned insulator layer 502. In at least some embodiments, one or more terminals are deposited on the lead such that at least a portion of each terminal is deposited over one or more exposed regions of a conductor in proximity to the proximal end of the lead 402.

Figure 6:
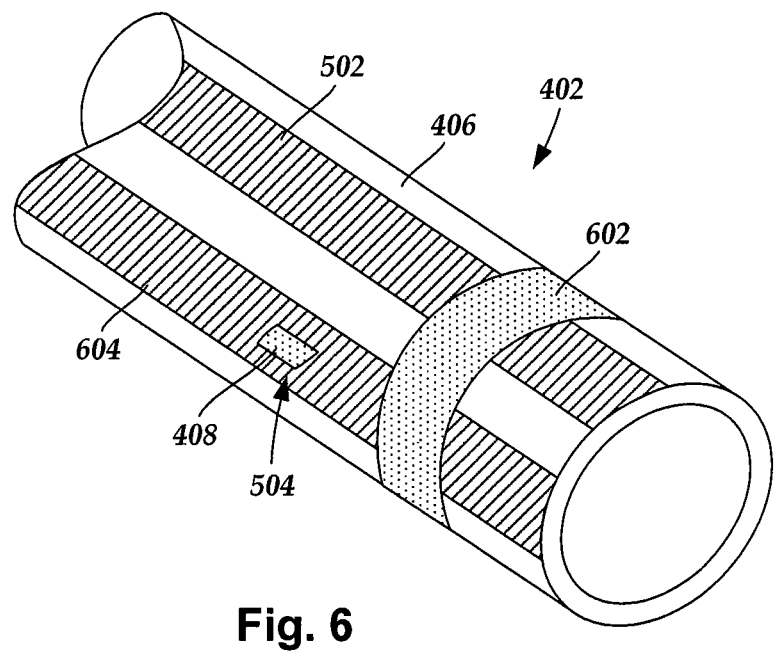
FIG. 6 is a schematic perspective view of one embodiment of a portion of the proximal end of the lead shown in FIG. 5, the lead including an insulator layer disposed over two conductors so that a region of both conductors remains exposed through the insulator layer, the lead also including a patterned terminal layer deposited on the lead and electrically coupled to one of the conductors via the exposed region of the conductor, according to the invention.

FIG. 6 is a schematic perspective view of one embodiment of a portion of the proximal end of the lead 402. The lead 402 includes a patterned terminal layer deposited over one of the exposed regions (504 in FIG. 5) of one of the conductors (408 in FIG. 4) to form a terminal 602 that is electrically coupling the terminal 602 to the conductor (408 in FIG. 4). Additionally, in FIG. 6 the exposed regions 504 are arranged in a staggered orientation such that additional terminals may be deposited over additional exposed regions 504 of other conductors 408 to electrically couple each conductor 408 to at least one terminal to form an array of terminals.

The terminal 602 may be formed using any suitable conductive biocompatible materials suitable for implantation into a patient using a deposition process including, for example, gold, platinum, platinum/iridium, stainless steel, MP35N, and the like or combinations thereof. In some embodiments, the terminal 602 may be deposited as a single conductive layer. In other embodiments, the terminal 602 may be deposited in multiple conductive layers. In at least some embodiments, each of the one or more conductive layers forming the terminal 602 has a thickness no greater than one micrometer. In at least some embodiments, each conductive layer has a thickness no greater than one hundred nanometers. In at least some embodiments, the terminal 602 is formed using a metallic deposition process, such as a physical or chemical vapor deposition, or the like. In at least some embodiments, the terminal 602 is formed using a sputtering process, such as a magnetron sputtering process, or the like. In at least some embodiments, the terminal 602 is formed directly on the one or more patterned insulator layers 502 and 604. In other embodiments, the terminal 602 is formed on one or more intermediate layers which, in turn, are disposed on the one or more patterned insulator layers 502 and 604. In at least some embodiments, the terminal 602 is at least partially formed directly on the inner core substrate 406.

Any suitable number of terminals may be formed on the lead 402. For example, there may be one, two, three, four, five, six, seven, eight, nine, ten, eleven, twelve, sixteen, twenty-four, thirty-two, or more terminals formed on the lead 402. It will be understood that other numbers of terminals may be formed on the lead 402. In at least some embodiments, the number of terminals formed on the lead 402 is proportional to the number of electrodes or conductors disposed on the lead 402. In at least some embodiments, the number of terminals formed on the lead 402 is equal to the number of electrodes or conductors disposed on the lead 402.

In at least some embodiments, once the one or more patterned insulator layers 502 are disposed over one or more conductors, one or more patterned electrode layers may be disposed on the lead to form one or more electrodes. In at least some embodiments, one or more electrodes may be electrically coupled to each of the conductors disposed beneath the patterned insulator layer. In at least some embodiments, one or more electrodes may be electrically coupled to each of the conductors via one or more regions of the conductors exposed through the patterned insulator layer. In at least some embodiments, one or more electrodes may be deposited on the lead such that at least a portion of each electrode is deposited over at least a portion of the patterned insulator layer 502. In at least some embodiments, one or more electrodes are deposited on the lead such that at least a portion of each electrode is deposited over one or more exposed regions of a conductor in proximity to the distal end of the lead 402.

Figure 7:
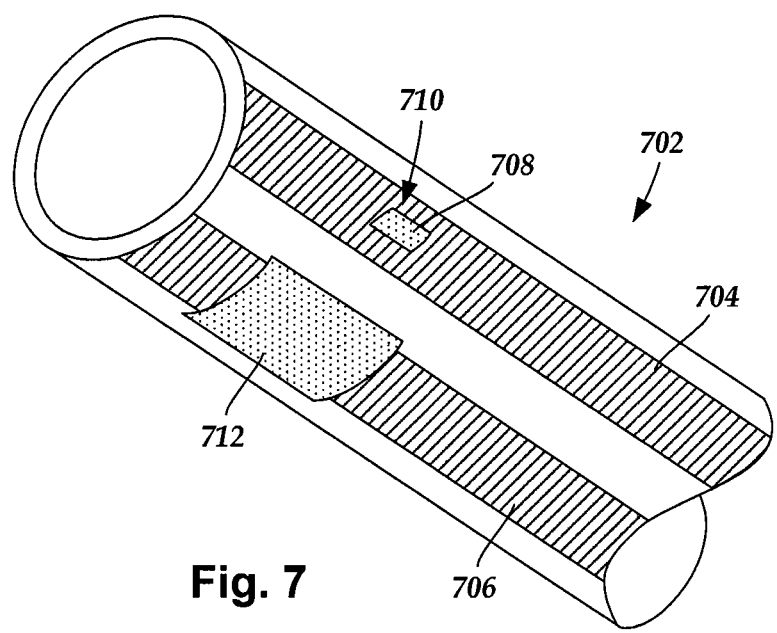
FIG. 7 is a schematic perspective view of one embodiment of a portion of a distal end of a lead, the lead including an insulator layer disposed over two deposited conductors so that a region of both conductors remains exposed through the insulator layer, the lead also including a patterned electrode layer deposited on the lead and electrically coupled to one of the conductors via the exposed region of the conductor, according to the invention.

FIG. 7 is a schematic perspective view of one embodiment of a portion of a distal end of a lead 702. The lead 702 includes two patterned insulator layers 704 and 706. A conductor 708 includes an exposed region 710 through the patterned insulator layer 704. A patterned electrode layer is deposited on the lead 702 to form an electrode 712. At least a portion of the electrode 712 is formed over an exposed region (see e.g., 710) of a conductor (see e.g., 708) beneath the patterned insulator layer 706 to electrically couple the electrode 712 to the conductor (see e.g., 708).

The electrode 712 may be formed using any suitable conductive biocompatible materials suitable for implantation into a patient using a deposition process including, for example, gold, platinum, platinum/iridium, stainless steel, MP35N, and the like or combinations thereof. In some embodiments, the electrode 712 may be deposited as a single conductive layer. In other embodiments, the electrode 712 may be deposited in multiple conductive layers. In at least some embodiments, each of the one or more conductive layers forming the electrode 712 has a thickness no greater than one micrometer. In at least some embodiments, each conductive layer has a thickness no greater than one hundred nanometers. In at least some embodiments, the electrode 712 is formed using a metallic deposition process, such as a physical or chemical vapor deposition, or the like. In at least some embodiments, the electrode 712 is formed using a sputtering process, such as a magnetron sputtering process, or the like. In at least some embodiments, the electrode 712 is formed directly on the one or more patterned insulator layers 502 and 604. In other embodiments, the electrode 712 is formed on one or more intermediate layers which, in turn, are disposed on the one or more patterned insulator layers 502 and 604. In at least some embodiments, the electrode 712 is at least partially formed directly on the inner core substrate 406.

Any suitable number of electrodes may be formed on the lead 702. For example, there may be one, two, three, four, five, six, seven, eight, nine, ten, eleven, twelve, sixteen, twenty-four, thirty-two, or more electrodes formed on the lead 702. It will be understood that other numbers of electrodes may be formed on the lead 702. In at least some embodiments, the number of electrodes formed on the lead 702 is proportional to the number of terminals or conductors disposed on the lead 702. In at least some embodiments, the number of electrodes formed on the lead 702 is equal to the number of terminals or conductors disposed on the lead 702.

In at least some embodiments, forming electrodes by depositing one or more patterned electrode layers on the lead 702 may allow a higher density of electrodes to be achieved at the distal end of the lead 702 than for leads with electrodes conventionally disposed at the distal end of a lead. Employing electrical stimulation systems with leads with an increased electrode density may make it possible to target patient tissue more precisely than with leads equipped with conventional electrodes. Increased stimulation precision may be especially beneficial for certain types of stimulation, for example, spinal cord stimulation, deep brain stimulation, erectile-dysfunction stimulation, and the like.

In at least some embodiments, electrodes may be formed on the lead 702 in many different shapes including, for example, cylindrical, segmented, circular, ovoid, triangular, rectangular, pentagonal, hexagonal, heptagonal, octagonal, nonagonal, decagonal, and the like. It will be understood that other electrode shapes of may be formed as well, including both regular and irregular shapes.

Figure 8A:
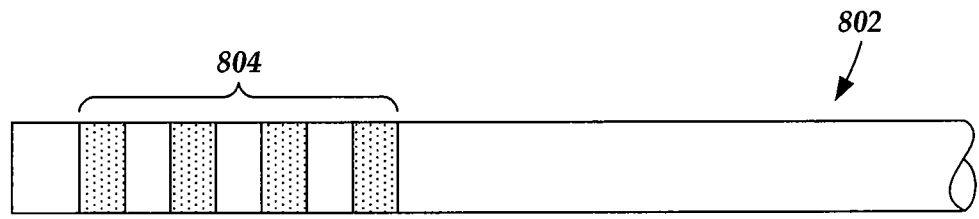
FIG. 8A is a schematic side view of one embodiment of a portion of a distal end of a percutaneous lead, the percutaneous lead including a deposited electrode layer patterned into cylindrical electrodes on the percutaneous lead, according to the invention.
Figure 8B:
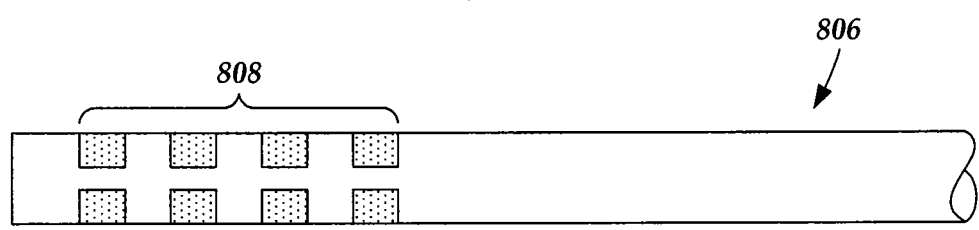
FIG. 8B is a schematic side view of one embodiment of a portion of a distal end of a percutaneous lead, the percutaneous lead including a deposited electrode layer patterned into segmented electrodes on the percutaneous lead, according to the invention.

FIG. 8A is a schematic side view of one embodiment of a portion of a distal end of a percutaneous lead 802. The percutaneous lead 802 includes cylindrical electrodes 804 formed on the percutaneous lead 802. FIG. 8B is a schematic side view of one embodiment of a portion of a distal end of a percutaneous lead 806. The percutaneous lead 806 includes segmented electrodes 808 formed on the percutaneous lead 806. In at least some embodiments, the percutaneous leads 802 and 806 may include a plurality of differently-shaped electrodes. For example, one or more of the percutaneous leads 802 and 806 may include a combination of both cylindrical electrodes and segmented electrodes.

Figure 9A:
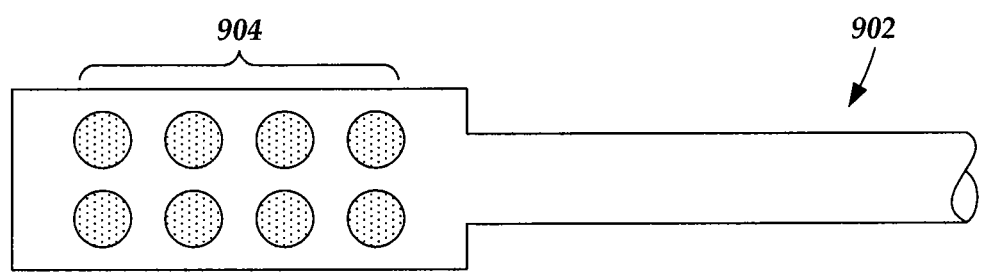
FIG. 9A is a schematic side view of one embodiment of a portion of a distal end of a paddle lead, the paddle lead including a deposited electrode layer patterned into circular electrodes on the paddle lead, according to the invention.
Figure 9B:
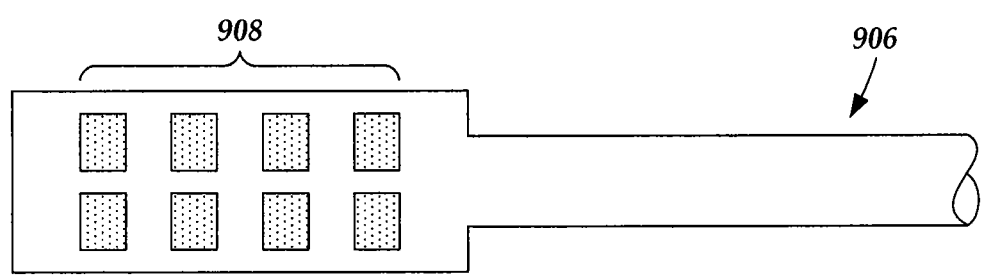
FIG. 9B is a schematic side view of one embodiment of a portion of a distal end of a paddle lead, the paddle lead including a deposited electrode layer patterned into rectangular electrodes on the paddle lead, according to the invention.

FIG. 9A is a schematic side view of one embodiment of a portion of a distal end of a paddle lead 902. The paddle lead 902 includes circular electrodes 904 formed on the paddle lead 902. FIG. 9B is a schematic side view of one embodiment of a portion of a distal end of a paddle lead 906. The paddle lead 906 includes rectangular electrodes 908 formed on the paddle lead 906. In at least some embodiments, the paddle leads 902 and 906 may include a plurality of differently-shaped electrodes. For example, one or more of the paddle leads 902 and 906 may include a combination of both circular electrodes and rectangular electrodes.

Figure 10:
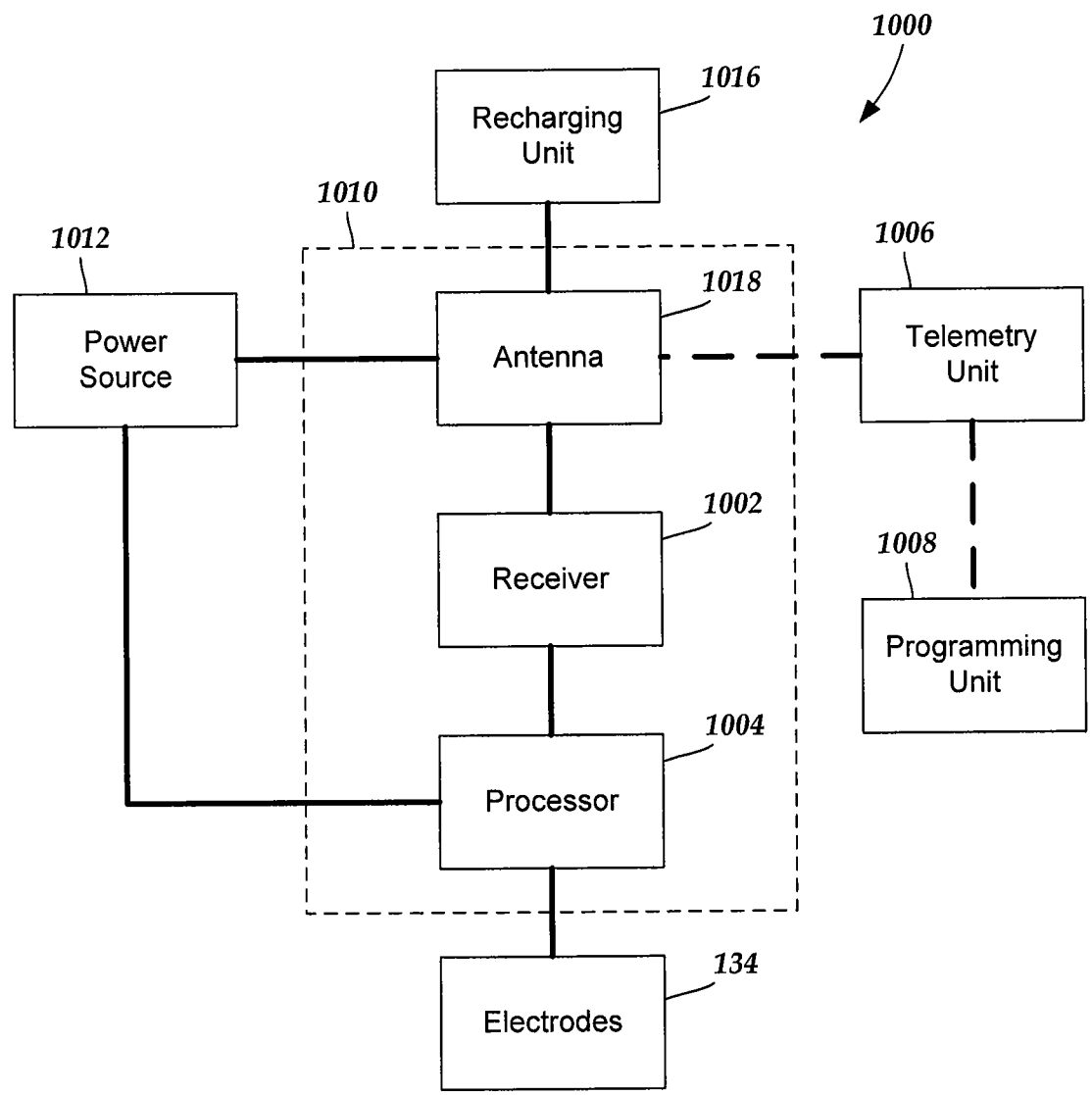
FIG. 10 is a schematic overview of one embodiment of components of a stimulation system, including an electronic subassembly disposed within a control module, according to the invention.

FIG. 10 is a schematic overview of one embodiment of components of an electrical stimulation system 1000 including an electronic subassembly 1010 disposed within a control module. It will be understood that the electrical stimulation system can include more, fewer, or different components and can have a variety of different configurations including those configurations disclosed in the stimulator references cited herein.

Some of the components (for example, power source 1012, antenna 1018, receiver 1002, and processor 1004) of the electrical stimulation system can be positioned on one or more circuit boards or similar carriers within a sealed housing of an implantable pulse generator, if desired. Any power source 1012 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 1018 or a secondary antenna. The external power source can be in a device that is mounted on the skin of the user or in a unit that is provided near the user on a permanent or periodic basis.

If the power source 1012 is a rechargeable battery, the battery may be recharged using the optional antenna 1018, if desired. Power can be provided to the battery for recharging by inductively coupling the battery through the antenna to a recharging unit 1016 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1004 is generally included to control the timing and electrical characteristics of the electrical stimulation system. For example, the processor 1004 can, if desired, control one or more of the timing, frequency, strength, duration, and waveform of the pulses. In addition, the processor 1004 can select which electrodes can be used to provide stimulation, if desired. In some embodiments, the processor 1004 may select which electrode(s) are cathodes and which electrode(s) are anodes. In some embodiments, the processor 1004 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1008 that, for example, allows modification of pulse characteristics. In the illustrated embodiment, the processor 1004 is coupled to a receiver 1002 which, in turn, is coupled to the optional antenna 1018. This allows the processor 1004 to receive instructions from an external source to, for example, direct the pulse characteristics and the selection of electrodes, if desired.

In one embodiment, the antenna 1018 is capable of receiving signals (e.g., RF signals) from an external telemetry unit 1006 which is programmed by a programming unit 1008. The programming unit 1008 can be external to, or part of, the telemetry unit 1006. The telemetry unit 1006 can be a device that is worn on the skin of the user or can be carried by the user and can have a form similar to a pager, cellular phone, or remote control, if desired. As another alternative, the telemetry unit 1006 may not be worn or carried by the user but may only be available at a home station or at a clinician's office. The programming unit 1008 can be any unit that can provide information to the telemetry unit 1006 for transmission to the electrical stimulation system 1000. The programming unit 1008 can be part of the telemetry unit 806 or can provide signals or information to the telemetry unit 1006 via a wireless or wired connection. One example of a suitable programming unit is a computer operated by the user or clinician to send signals to the telemetry unit 1006.

The signals sent to the processor 1004 via the antenna 1018 and receiver 1002 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1000 to cease operation, to start operation, to start charging the battery, or to stop charging the battery. In other embodiments, the stimulation system does not include an antenna 1018 or receiver 1002 and the processor 1004 operates as programmed.

Optionally, the electrical stimulation system 1000 may include a transmitter (not shown) coupled to the processor 1004 and the antenna 1018 for transmitting signals back to the telemetry unit 1006 or another unit capable of receiving the signals. For example, the electrical stimulation system 1000 may transmit signals indicating whether the electrical stimulation system 1000 is operating properly or not or indicating when the battery needs to be charged or the level of charge remaining in the battery. The processor 1004 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable lead comprising:
   a lead body with a distal end portion, a proximal end portion, and an inner core substrate having a surface, the lead body configured and arranged for implanting into a patient;
   a plurality of conductors attached directly to the surface of the inner core substrate by deposition, each conductor comprising at least one layer of at least one conductive material extending between the proximal end portion and the distal end portion of the lead body;
   a patterned insulator layer distinct from the inner core substrate, the patterned insulator layer attached directly to the plurality of conductors such that each conductor of the plurality of conductors is sandwiched between the inner core substrate and the patterned insulator layer, the patterned insulator layer attached to the plurality of conductors such that at least two regions of each conductor of the plurality of conductors remain exposed through the insulator layer, including a first exposed region at the proximal end portion of the lead body and a second exposed region at the distal end portion of the lead body;
   a patterned terminal layer, defining a plurality of separated terminals, attached by deposition to the proximal end portion of the lead body, wherein for each conductor of the plurality of conductors at least one terminal of the plurality of separated terminals is attached by deposition to the conductor via the first exposed region of that conductor, wherein each terminal of the plurality of separated terminals is attached by deposition to at least one of a portion of the patterned insulator layer or the inner core substrate along the proximal end portion of the lead body; and
   a patterned electrode layer, defining a plurality of separated electrodes, attached by deposition to the distal end portion of the lead body, wherein for each conductor of the plurality of conductors at least one electrode of the plurality of separated electrodes is attached by deposition to the conductor via the second exposed region of that conductor, wherein each electrode of the plurality of separated is attached by deposition to at least one of a portion of the patterned insulator layer or the inner core substrate along the distal end portion of the lead body.

2. The lead of claim 1, wherein the lead body defines at least one lumen, the at least one lumen extending from the proximal end of the lead body to the distal end of the lead body.

3. The lead of claim 1, wherein the patterned terminal layer has a thickness that is no greater than one hundred nanometers.

4. The lead of claim 1, wherein the patterned electrode layer has a thickness that is no greater than one hundred nanometers.

5. The lead of claim 1, wherein the patterned insulator layer comprises at least one non-conductive polymer.

6. An electrical stimulating system comprising:
the implantable lead of claim 1;
a control module configured and arranged to electrically couple to the proximal end portion of the lead body of the lead, the control module comprising
a housing, and
an electronic subassembly disposed in the housing; and
a connector for receiving the lead body, the connector comprising
a connector housing defining a port configured and arranged for receiving the proximal end portion of the lead body, and
a plurality of conductive contacts disposed in the connector housing, the conductive contacts configured and arranged to couple to at least one of the plurality of terminals disposed on the proximal end portion of the lead body.

7. The electrical stimulating system of claim 6, further comprising a lead extension having a distal end and a proximal end, the connector disposed on the distal end of the lead extension.

8. The electrical stimulating system of claim 7, wherein the proximal end of the lead extension is configured and arranged for insertion into another connector.

9. The electrical stimulating system of claim 7, wherein the lead extension comprises
an inner core substrate extending from the distal end of the lead extension to the proximal end of the lead extension;
a plurality of lead extension conductors disposed on the inner core substrate, each lead extension conductor comprising at least one layer of at least one conductive material deposited on the inner core substrate;
a patterned insulator layer disposed over the lead extension conductors such that at least one region of each lead extension conductor remains exposed through the patterned insulator layer, including at least one region in proximity to the proximal end of the lead extension; and
a patterned terminal layer, defining a plurality of separated terminals, deposited at the proximal end of the lead extension, wherein for each lead extension conductor of the plurality of lead extension conductors at least one terminal of the plurality of separated terminals is electrically coupled to the lead extension conductor via the at least one region of the lead extension conductor exposed through the patterned insulator layer in proximity to the proximal end of the lead extension.

10. The electrical stimulating system of claim 9, wherein the patterned terminal layer of the lead extension has a thickness that is no greater than one hundred nanometers.

11. The electrical stimulating system of claim 6, wherein the patterned electrode layer has a thickness that is no greater than one hundred nanometers.

12. A method for making an implantable lead, the method comprising:
attaching, by deposition, a plurality of conductors directly to a surface of an inner core substrate of a lead body of the lead, wherein each conductor of the plurality of conductors comprises at least one layer of at least one conductive material extending between a proximal end portion and a distal end portion of the lead body;
attaching a patterned insulator layer that is distinct from the inner core substrate directly to the plurality of conductors such that each conductor of the plurality of conductors is sandwiched between the inner core substrate and the patterned insulator layer, the patterned insulator layer attached to the plurality of conductors such that at least two regions of each conductor of the plurality of conductors remains exposed through the insulator layer, including a first exposed region at the proximal end portion of the lead body and a second exposed region at the distal end portion of the lead body;
attaching, by deposition, a patterned terminal layer, defining a plurality of separated terminals, to the proximal end portion of the lead body, wherein for each conductor of the plurality of conductors at least one terminal of the plurality of separated terminals is attached by deposition to the conductor via the first exposed region of that conductor, wherein each terminal of the plurality of separated terminals is attached by deposition to at least one of a portion of the patterned insulator layer or the inner core substrate along the proximal end portion of the lead body; and
attaching, by deposition, a patterned electrode layer, defining a plurality of separated electrodes, to the distal end portion of the lead body, wherein for each conductor of the plurality of conductors at least one electrode of the plurality of separated electrodes is attached by deposition to the conductor via the second exposed region of that conductor, wherein each electrode of the plurality of separated electrodes is attached by deposition to at least one of a portion of the patterned insulator layer or the inner core substrate along the distal end portion of the lead body.

13. The method of claim 12, wherein attaching, by deposition, the plurality of conductors comprises sputtering a conductive material over a portion of the surface of the inner core substrate to form the plurality of conductors.

14. The method of claim 12, wherein attaching, by deposition, the patterned terminal layer comprises sputtering a conductive material over a portion of the surface of the inner core substrate to form the plurality of conductors.

15. The method of claim 12, wherein attaching, by deposition, the patterned electrode layer comprises sputtering a conductive material over a portion of the surface of the inner core substrate to form the plurality of conductors.

16. The method of claim 12, wherein attaching the patterned insulator layer directly to the plurality of conductors comprises spray coating the patterned insulator layer over at least a portion of each conductor of the plurality of conductors.

17. The method of claim 12, wherein attaching the patterned insulator layer directly to the plurality of conductors comprises printing the patterned insulator layer over at least a portion of each conductor of the plurality of conductors using an ink jet printer.

18. The method of claim 12, wherein attaching the patterned insulator layer directly to the plurality of conductors comprises disposing the patterned insulator over at least a portion of each conductor of the plurality of conductors individually.

19. The method of claim 12, wherein attaching the patterned insulator layer directly to the plurality of conductors comprises masking at least one of the regions of at least one of the conductors of the plurality of conductors to remain exposed through the patterned insulator layer prior to application of the patterned insulator layer.

20. The lead of claim 1, wherein the patterned terminal layer is attached by deposition directly to at least one portion of the patterned insulation layer along the proximal end portion of the lead body.

* * * * *